United States Patent
Wang et al.

(10) Patent No.: US 11,511,018 B2
(45) Date of Patent: Nov. 29, 2022

(54) CONDUCTIVE BIOMIMETIC SKIN SCAFFOLD MATERIAL WITH SELF-REPAIRING FUNCTION AND A METHOD OF PREPARING THE SAME

(71) Applicants: Xuechuan Wang, Xi'an (CN); Manhui Zheng, Xi'an (CN); Xinhua Liu, Xi'an (CN); Ouyang Yue, Xi'an (CN); Mengdi Hou, Xi'an (CN); Youyou Wang, Xi'an (CN)

(72) Inventors: Xuechuan Wang, Xi'an (CN); Manhui Zheng, Xi'an (CN); Xinhua Liu, Xi'an (CN); Ouyang Yue, Xi'an (CN); Mengdi Hou, Xi'an (CN); Youyou Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 154 days.

(21) Appl. No.: 17/203,689

(22) Filed: Mar. 16, 2021

(65) Prior Publication Data
US 2022/0023507 A1 Jan. 27, 2022

(30) Foreign Application Priority Data
Jul. 23, 2020 (CN) .......................... 202010716078.9

(51) Int. Cl.
*A61L 27/60* (2006.01)
*A61L 27/26* (2006.01)
(Continued)

(52) U.S. Cl.
CPC ................ *A61L 27/60* (2013.01); *A61L 27/08* (2013.01); *A61L 27/26* (2013.01); *B29B 7/90* (2013.01);
(Continued)

(58) Field of Classification Search
CPC .................................. A61L 27/60; A61L 27/08
See application file for complete search history.

(56) References Cited

U.S. PATENT DOCUMENTS

| | | | |
|---|---|---|---|
| 6,703,041 B2 * | 3/2004 | Burns | A61L 31/041 424/443 |
| 2005/0020506 A1 * | 1/2005 | Drapeau | A61L 24/0005 424/130.1 |

(Continued)

OTHER PUBLICATIONS

Shahini, A., https://www.ncbi.nlm.nih.gov/pmc/articles/PMC3875523/ (Year: 2014).*

*Primary Examiner* — Nicholas R Krasnow

(57) ABSTRACT

A method for preparing a conductive biomimetic skin scaffold material with self-repairing function includes the following steps: adding 1-(3-dimethylaminopropyl)-3-ethyl-carbodiimide hydrochloride to a homogeneous dispersion of acidified carbon nanotubes, poly(3,4-ethylenedioxythiophene) polystyrene sulfonate (PEDOT:PSS), and gelatin to cross-link to obtain a conductive composite colloid; and injecting the conductive composite colloid into a mold, aging at −4-4° C. for 12-24 hours, and then soaking in a phosphate-buffered saline (PBS) solution with a pH of 7.0-7.4 for 12-24 hours to obtain the conductive biomimetic skin scaffold material.

6 Claims, 4 Drawing Sheets

(51) Int. Cl.
*A61L 27/08* (2006.01)
*B29B 7/90* (2006.01)
*B29C 45/00* (2006.01)
B29K 507/04 (2006.01)
B29L 31/00 (2006.01)
B29K 105/16 (2006.01)

(52) U.S. Cl.
CPC ....... *B29C 45/0001* (2013.01); *A61L 2400/12* (2013.01); *B29K 2089/00* (2013.01); *B29K 2105/167* (2013.01); *B29K 2507/04* (2013.01); *B29L 2031/7532* (2013.01)

(56) References Cited

U.S. PATENT DOCUMENTS

| | | | | |
|---|---|---|---|---|
| 2016/0053231 | A1* | 2/2016 | Xu | C12N 5/0697 435/402 |
| 2017/0319750 | A1* | 11/2017 | Grinberg | A61L 27/12 |
| 2018/0078423 | A1* | 3/2018 | Magin | A61F 13/00063 |
| 2020/0054786 | A1* | 2/2020 | Liu | A61L 27/20 |
| 2022/0205055 | A1* | 6/2022 | Harder | C12Q 1/6851 |

* cited by examiner

CONDUCTIVE BIOMIMETIC SKIN SCAFFOLD MATERIAL WITH SELF-REPAIRING FUNCTION AND A METHOD OF PREPARING THE SAME

The present invention claims priority to Chinese Patent Application No. CN 202010716078.9, filed on Jul. 23, 2020, which is incorporated by reference for all purposes as if fully set forth herein.

FIELD OF THE INVENTION

The present invention discloses a conductive biomimetic skin scaffold material with self-repairing function and a method of preparing the same.

BACKGROUND OF THE INVENTION

Skin is the largest organ of the human body and is a barrier between the human body and the external environment. Skin barrier refers to the natural line of defense composed of the sebum and stratum corneum on the surface of the skin, which can effectively defend against external stimuli and also lock the moisture in the skin. In real life, skin injury can be caused by burns, trauma, diabetes, chronic ulcers, etc., and the human body cannot completely self-heal any full-thickness skin defects larger than 4 cm in diameter.

Tissue engineered skin uses a three-dimensional scaffold as a carrier and is obtained by planting cells on the scaffold, which can fundamentally solve the problem of rebuilding or repairing the skin barrier and has a good development prospect. As one of the three elements of tissue engineering, scaffold materials can be divided into synthetic material and biological material according to their chemical properties. Synthetic scaffold materials are mostly polyesters, such as polylactic acid, poly-L-lactic acid, and polyglycolic acid. The biggest problem with synthetic material is the lack of cell signal recognition, which is not conducive to cell adhesion and the activation of specific genes. It requires grafting specific recognition site (RGD sequence) on the surface of the material to increase the cellular biological activity of the scaffold, thereby increasing the cost and difficulty of making scaffold materials. Chitin, chitosan, alginate, collagen, hyaluronic acid, gelatin, agar and other natural polymers have the same or similar structure to the extracellular matrix, which can promote cell adhesion, proliferation and differentiation, so they are often used as biological scaffold materials. The biological materials have a wide range of sources, simple to produce and low price. However, they also have problems, such as poor mechanical properties, uncertain antigenicity elimination, and unsuitable control of the degradation rate.

On the other hand, there is an electric field in living tissues. The trans-epidermal voltage is between 20-50 mV, and the skin epidermal voltage is low. Normally, when an injury occurs, a "damage current" is generated between the deep tissue and the skin surface. Studies have shown that the "damage current" may attract cells involved in repair, change the permeability of cell membranes, increase cell secretion products and direct the re-plasticization of cell structures. Research on the application of microcurrent to various skin trauma treatments shows that microcurrent can activate the regeneration process of myocardium and other tissues. The regulation mechanism is: (1) increasing the secretion of BMP6; (2) down-regulating the activity of nuclear factor rd3; and (3) up-regulating the expression of vascular endothelial growth factor mRNA.

SUMMARY OF THE INVENTION

In summary, first, an ideal tissue scaffold should have the following characteristics: (1) good biocompatibility, no obvious rejection and inflammation, and no risk of disease transmission; (2) allowing cells to re-attach on the surface and promoting cell proliferation and differentiation; (3) suitable degradation rate, degradation products being non-toxic or easily absorbed and eliminated in time; (4) a three-dimensional structure with high porosity for cell adhesion and extracellular matrix and enough space for regeneration and cell diffusion; (5) a certain mechanical strength, resisting certain tissue stress and playing a role of support and template.

Second, considering the effect of microcurrent on stimulating tissue regeneration, a conductive biomimetic skin scaffold material is proposed. The conductive biomimetic skin scaffold material can enhance the effect of microcurrent by regularly loading an external power source and promote cell proliferation. The conductive biomimetic skin scaffold material achieves the purpose of promoting cell regeneration by transmitting microcurrent.

Further, in the process of cell adhesion and proliferation, the scaffold material will inevitably produce damage and micro-cracks under the action of tissue stress, which will cause macroscopic cracks and breakage. If we can repair such early damages and cracks, it is of great significance to eliminate safety hazards, enhance material strength and service life. Providing the scaffold material self-repairing ability can greatly improve its service life and functional reliability. Therefore, the self-repairing function of the scaffold material is further required.

The present invention uses a gelatin extracted from the dermal matrix of decellularized fetal cowhide which has better biological safety as a substrate. The gelatin is compounded with non-cytotoxic conductive polymer poly3,4-ethylenedioxythiophene:polyphenylene Ethylene sulfonate (PEDOT:PSS) solution and acidified carbon nanotubes (H-MWCNTs). 1-(3-Dimethylaminopropyl)-3-ethylcarbodiimide hydrochloride (EDC) is added to initiate a cross-linking reaction to prepare the scaffold material. The gelatin contains a large number of RDG sequences and functional groups, which can promote cell adhesion and growth; the PEDOT:PSS solution has high conductivity and can improve the conductivity of the material; and the acidified carbon nanotubes can not only improve the conductivity of the material, but also serve as a reinforced filler of the gel scaffold to improve the mechanical properties of the scaffold material. The mechanical strength of the scaffold material after EDC cross-linking is greatly improved, which is sufficient to cope with tissue stress. The scaffold material has good biocompatibility, high mechanical strength, and both self-repair performance and tissue regeneration and repair properties, and can be widely used in skin wound repair treatment.

The gelatin, as a hydrolyzed product of collagen, has the following advantages: (1) compared with collagen, the immunogenicity is greatly reduced; (2) high biocompatibility and degradability, and containing a large number of RGD sequences, which is beneficial to the development, adhesion and growth and the cells; (3) temperature reversibility and adjustable tensile strength and morphological structure; (4) a large number of different functional groups, which can be chemically modified or loaded with drugs to enhance its use value; (5) a wide range of sources, low price, and more practical application value.

In one embodiment, the present application provides a method for preparing a conductive biomimetic skin scaffold material with self-repairing function. The method includes the following steps: adding 1-(3-dimethylaminopropyl)-3-ethylcarbodiimide hydrochloride to a homogeneous dispersion of acidified carbon nanotubes, poly(3,4-ethylenedioxythiophene) polystyrene sulfonate (PEDOT:PSS), and gelatin to cross-link to obtain a conductive composite colloid; and injecting the conductive composite colloid into a mold, aging at −4-4° C. for 12-24 hours, and then soaking in a phosphate-buffered saline (PBS) solution with a pH of 7.0-7.4 for 12-24 hours to obtain the conductive biomimetic skin scaffold material.

In another embodiment, the method further includes dispersing 1.0-5.0 mL of a PEDOT:PSS solution and 1.0-5.0 mL of a 0.05-1.0 g/mL acidified carbon nanotube solution in 10.0-50.0 mL of water to obtain a mixture; adding 1.0-10.0 g of gelatin to the mixture to make the mixture evenly dispersed; adding 1.0-5.0 mL of a 0.02-0.5 g/mL 1-(3-dimethylaminopropyl)-3-ethylcarbodiimide hydrochloride aqueous solution to the mixture; and stirring the mixture at 30-60° C. to obtain the conductive composite colloid.

In another embodiment, the method further includes (1) adding 10.0-50.0 mL water, 1.0-5.0 mL a PEDOT:PSS solution, and 1.0-5.0 mL of a 0.05-1.0 g/mL acidified carbon nanotube solution to a reactor to form a mixture, and ultrasonicating the mixture at 50-100 W, 40 kHz, for 30-120 minutes; (2) adding 5.0-20.0 g of gelatin to the mixture, stirring the mixture at 30-60° C. for 30-120 minutes to evenly dispersing the mixture; and (3) dissolving 0.1-0.5 g of 1-ethyl-3-(3-dimethylaminopropyl)carbodiimide (EDC) powder in 1.0-5.0 mL water to obtain a 0.02-0.5 g/mL EDC solution; adding 0.1-2.0 mL of the EDC solution slowly to the mixture of step (2), stirring for 30-120 minutes to at 30-60° C. to obtain the conductive composite colloid.

In another embodiment, the gelatin is derived from a fetal bovine acellular dermal matrix.

In another embodiment, the method further includes reacting 1.0-5.0 g of multi-walled carbon nanotubes, 50.0-250.0 g of 98% concentrated $H_2SO_4$, and 20.0-100.0 g of 65-68% $HNO_3$ at 50-100° C. for 5-15 hours to obtain an acidified carbon nanotube solution.

In another embodiment, the method further includes centrifugating the acidified carbon nanotube solution at a speed of 1000 to 5000 rpm for 10-60 minutes, and filtering; adding 100.0-500.0 mL of water, centrifugating at 5000-8000 rpm for 10-60 minutes, and filtering; adding 100.0-500.0 mL of water, centrifugating at 8000-10000 rpm for 10-60 minutes; and freeze-drying to obtain the acidified carbon nanotubes.

Compared with the conventional technology, the present invention has the following advantages:

(1) The present invention uses gelatin extracted from the acellular dermal matrix of fetal cowhide after removing antigen as starting material. The gelatin molecule contains a large number of RGD sequences, which can promote cell adhesion and growth and induce cell proliferation and differentiation. It is an excellent bionic skin scaffold base material;

(2) The gelatin-based scaffold material prepared by the present invention has a three-dimensional structure with high porosity, thereby providing sufficient space for cell adhesion, extracellular matrix regeneration and cell diffusion. It has a certain mechanical strength and can resist certain stress and play a role of support and template;

(3) Compared with traditional scaffold materials, the scaffold material prepared by the present invention has the most obvious difference in electrical conductivity, and the microcurrent can promote cell growth, proliferation, and differentiation, increasing its advantages as scaffold materials;

(4) The scaffold material prepared by the present invention has good tensile properties and self-repair properties, can respond to the deformation and microcracks of tissue stress, self-repair, and is more conducive to protecting cell morphology and preventing cells from falling off the scaffold;

(5) The scaffold material prepared by the present invention contains a large number of active functional groups, which can be grafted and loaded with different types of growth factors and drugs to obtain a slow-release, temperature-sensitive multifunctional stent material, and has a novel application for postoperative repair and wound healing as smart medical materials.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
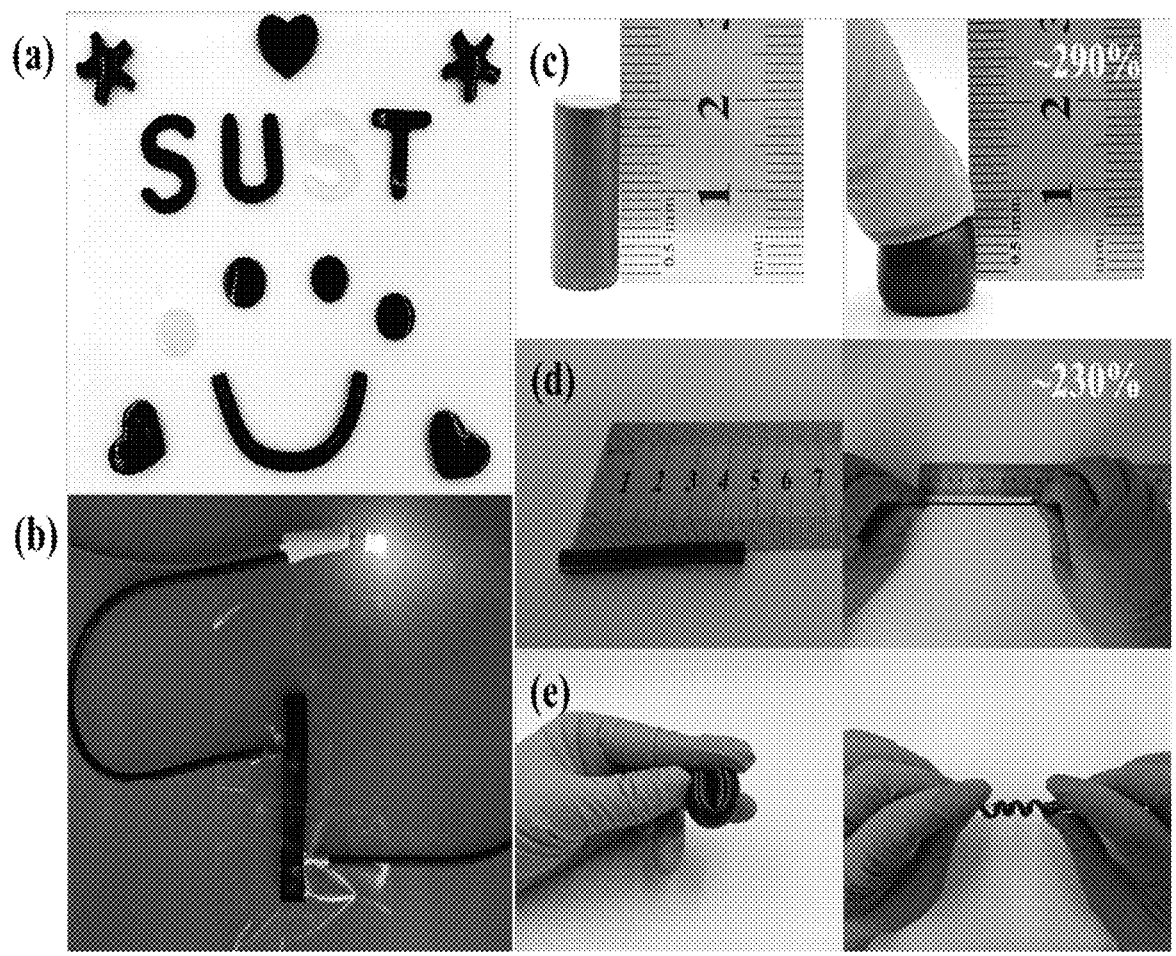
FIG. 1 shows a conductive biomimetic skin scaffold material: the material has good plasticity, conductivity, tensile and compression properties.

Reference will now be made in detail to embodiments of the present invention, example of which is illustrated in the accompanying drawings.

Example 1

(1) Preparation of acidified carbon nanotube dispersion: accurately weighing 1.0 g of multi-walled carbon nanotubes (MWCNTs), 50.0 g of concentrated $H_2SO_4$ (98%), and 100 g of HNO$_3$ (65-68%), placing them in a three-necked flask, and heating to 50° C. for 15 hours; after the reaction is complete, conducting gradient speed centrifugation, the conditions of gradient speed centrifugation: (1) centrifugating at 5000 rpm for 60 min and filtering; (2) adding 100.0 mL of ultrapure water, centrifugating at 8000 rpm for 60 min, and filtering; (3) adding 100.0 mL of ultrapure water, centrifugating at 10000 rpm for 60 min, repeating each centrifugation step 3 times, freeze-drying to obtain the acidified carbon nanotube powder; weighing 0.1 g of the acidified carbon nanotube powder and ultrasonicating it in 200 mL of H$_2$O for 0.5 h to prepare 0.05% (m/v) acidified carbon nanotube dispersion for later use;

(2) Preparation of acidified carbon nanotube/PEDOT:PSS composite dispersion: accurately measuring 10.0 mL of ultrapure water in a single-necked flask, and accurately pipetting 1.0 mL of PEDOT:PSS solution and 5.0 mL of 0.05% acidified carbon nanotube dispersion into the flask, ultrasonicating at 50 W, 40 kHz for 30 min;

(3) Preparation of gelatin-based composite conductive gel solution: accurately weighing 2.0 g of gelatin and adding mixture of step (2), heating up to 30° C., stirring at constant temperature for 30 minutes to completely dissolving the gelatin and uniformly disperse the resulted mixture;

(4) Preparation of 1-(3-dimethylaminopropyl)-3-ethylcarbodiimide hydrochloride (EDC) cross-linked gelatin-based composite conductive gel: accurately weighing 0.1 g of EDC powder and dissolving it in 5.0 mL of H$_2$O to obtain 2% (m/v) EDC solution; accurately pipetting 2.0 mL of 2% EDC solution and slowly adding into the composite solution system of step 3, and continuing to stir at a constant temperature for 30 minutes to obtain an EDC crosslinked modified gelatin-based composite conductive gel solution;

(5) Pouring the conductive gel solution of step (4) into a custom-made polytetrafluoroethylene mold, and placing it in a refrigerator at −4° C. for 24 h; the soaking it in a PBS solution with a pH of 7.0 for 12 h to obtain a conductive biomimetic skin scaffold material with self-repair function.

Figure 2:
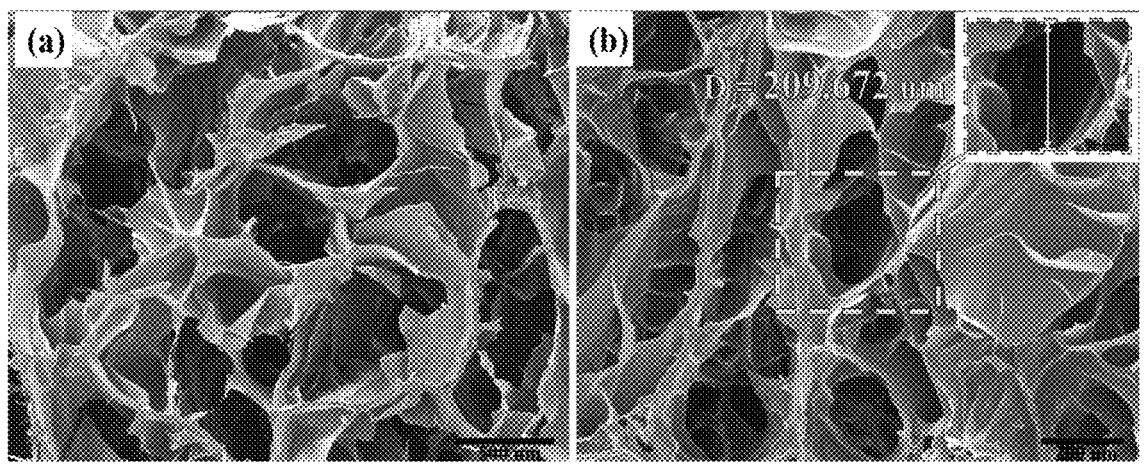
FIG. 2 is a scanning electron micrograph (SEM) of the conductive biomimetic skin scaffold material: the material has a porous structure with a pore size of about 200 μm, which can provide 3D space for the growth of skin tissue cells.
Figure 3:
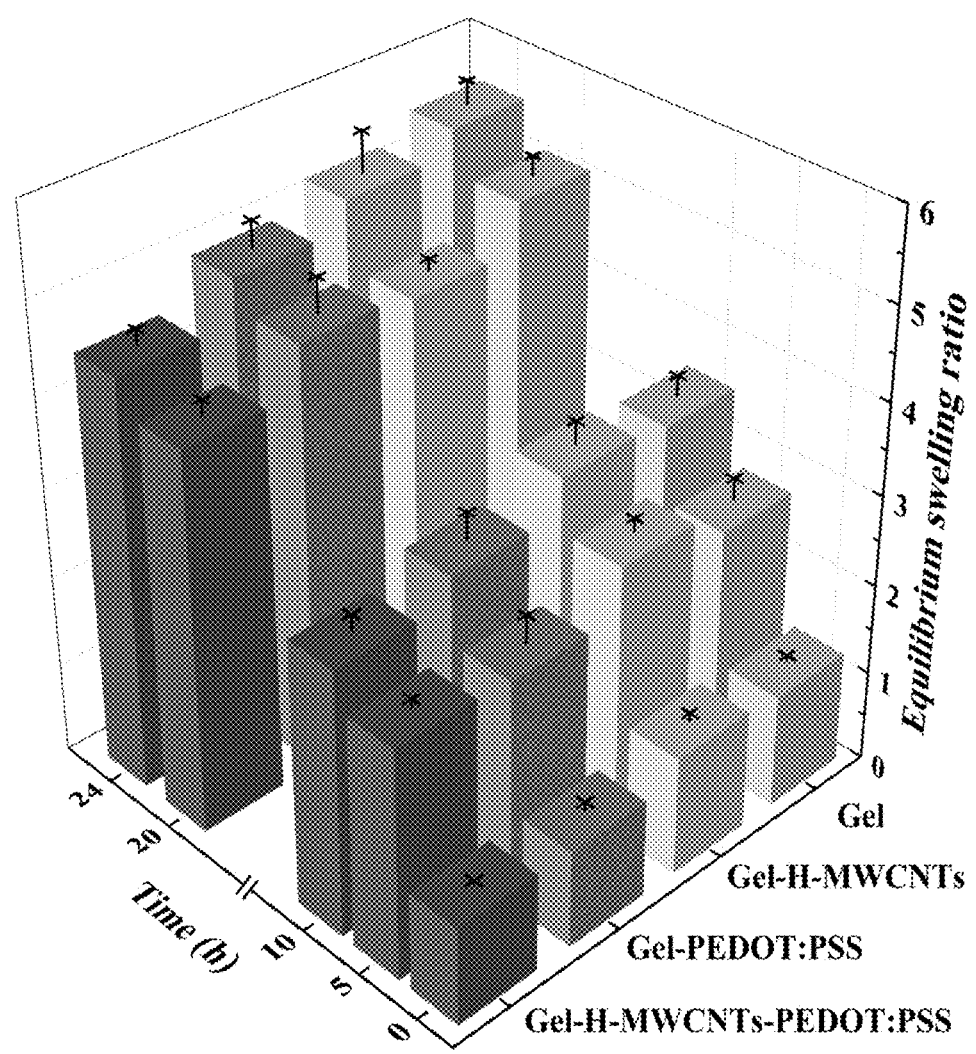
FIG. 3 is a diagram that shows in vitro swelling performance of the conductive biomimetic skin scaffold material: the material has good swelling performance, and can fully absorb wound exudate and reduce the risk of bacterial infection.
Figure 4:
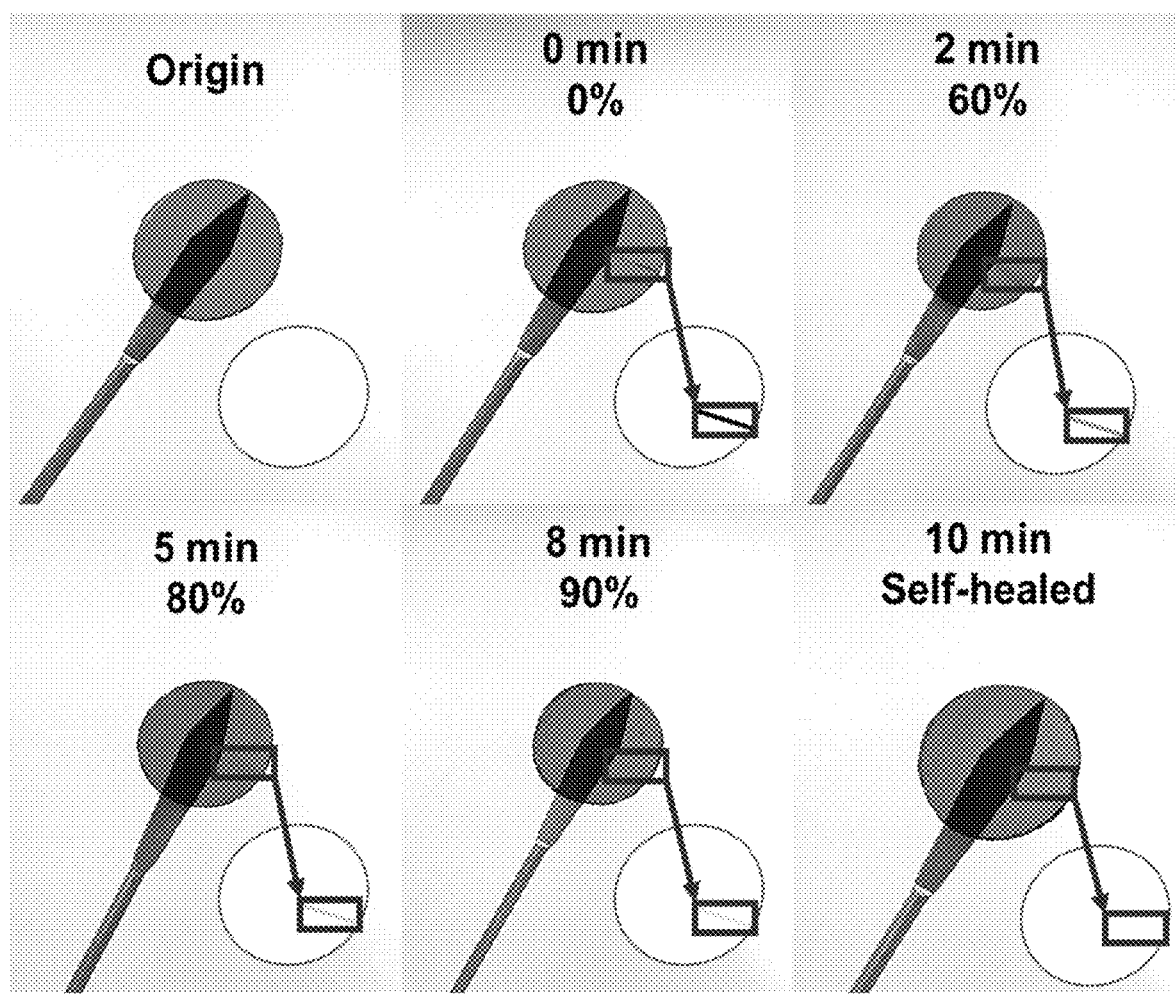
FIG. 4 shows the self-healing property of the conductive biomimetic skin scaffold material: cutting a circular shaped conductive biomimetic skin scaffold material in a radius direction, self-healing at 37° C., the material being almost completely healed after 10 minutes, indicating healing properties.
Figure 5:
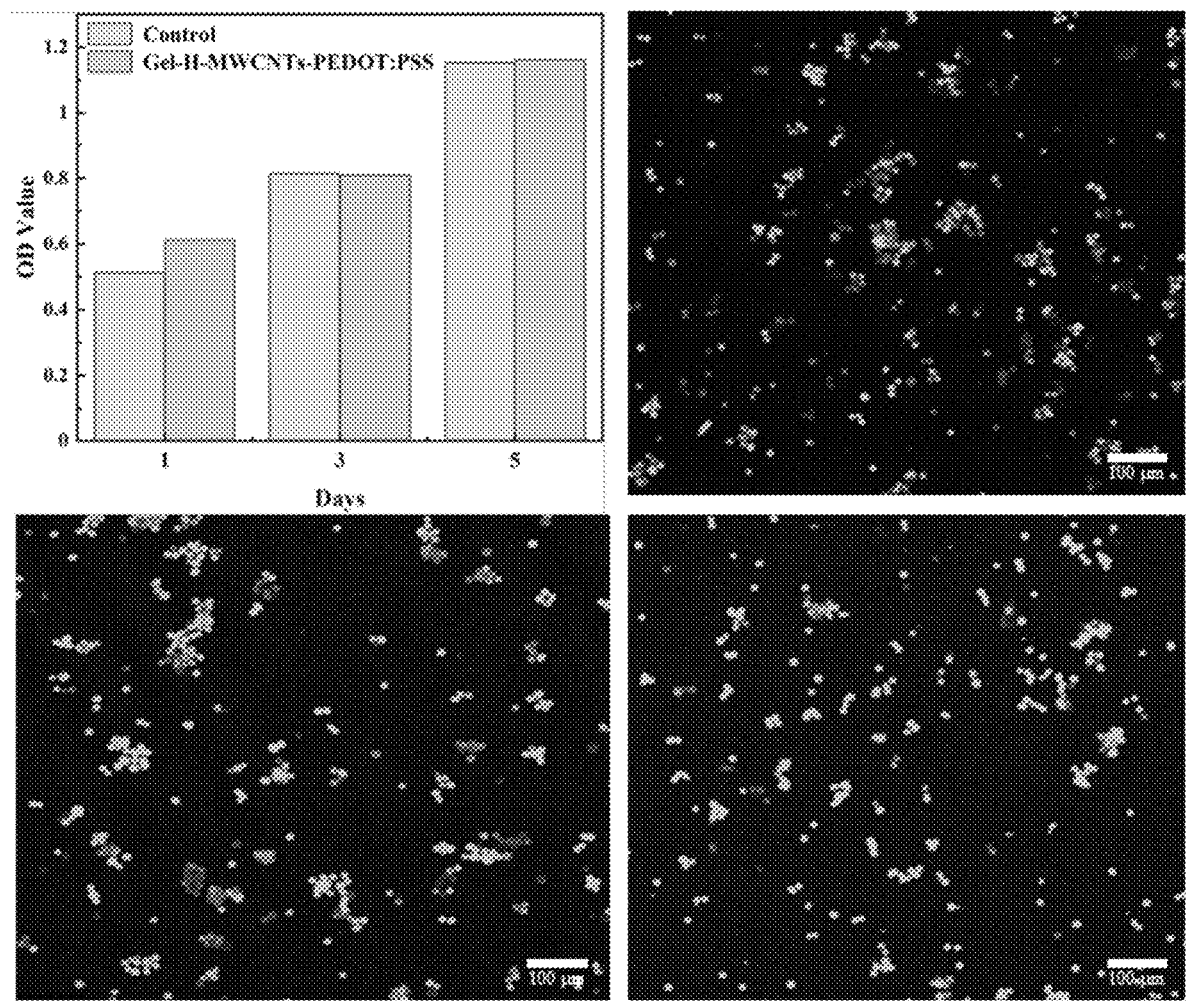
FIG. 5 shows the biocompatibility (MTT) test results of the conductive biomimetic skin scaffold material: the material has high biocompatibility.

FIG. 1 shows a conductive biomimetic skin scaffold material. The material has good plasticity, conductivity, tensile and compression properties. As shown in FIG. 2, the material has a porous structure with a pore size of about 200 μm, which can provide 3D space for the growth of skin tissue cells. As shown in FIG. 3, the material has good swelling performance, and can fully absorb wound exudate and reduce the risk of bacterial infection. As shown in FIG. 4, the material has self-healing property. As shown in FIG. 5, the material has high biocompatibility.

Example 2

(1) Preparation of acidified carbon nanotube dispersion: accurately weighing 3.0 g of multi-walled carbon nanotubes (MWCNTs), 50.0 g of concentrated H$_2$SO$_4$ (98%), and 20 g of HNO$_3$ (65-68%), placing them in a three-necked flask, and heating to 80° C. for 10 hours; after the reaction is complete, conducting gradient speed centrifugation, the conditions of gradient speed centrifugation: (1) centrifugating at 3000 rpm for 30 min and filtering; (2) adding 300.0 mL of ultrapure water, centrifugating at 6500 rpm for 30 min, and filtering; (3) adding 300.0 mL of ultrapure water, centrifugating at 9000 rpm for 30 min, repeating each centrifugation step 4 times, freeze-drying to obtain the acidified carbon nanotube powder; weighing 0.5 g of the acidified carbon nanotube powder and ultrasonicating it in 100 mL of H$_2$O for 1 h to prepare 0.5% (m/v) acidified carbon nanotube dispersion for later use;

(2) Preparation of acidified carbon nanotube/PEDOT:PSS composite dispersion: accurately measuring 50.0 mL of ultrapure water in a single-necked flask, and accurately pipetting 3.0 mL of PEDOT:PSS solution and 2.5 mL of 0.5% acidified carbon nanotube dispersion into the flask, ultrasonicating at 80 W, 40 kHz for 80 min;

(3) Preparation of gelatin-based composite conductive gel solution: accurately weighing 5.0 g of gelatin and adding mixture of step (2), heating up to 45° C., stirring at constant temperature for 60 minutes to completely dissolving the gelatin and uniformly disperse the resulted mixture;

(4) Preparation of 1-(3-dimethylaminopropyl)-3-ethylcarbodiimide hydrochloride (EDC) cross-linked gelatin-based composite conductive gel: accurately weighing 0.25 g of EDC powder and dissolving it in 2.5 mL of H$_2$O to obtain 10% (m/v) EDC solution; accurately pipetting 1.0 mL of 10% EDC solution and slowly adding into the composite solution system of step 3, and continuing to stir at a constant temperature for 60 minutes to obtain an EDC crosslinked modified gelatin-based composite conductive gel solution;

(5) Pouring the conductive gel solution of step (4) into a custom-made polytetrafluoroethylene mold, and placing it in a refrigerator at 0° C. for 18 h; the soaking it in a PBS solution with a pH of 7.2 for 18 h to obtain a conductive biomimetic skin scaffold material with self-repair function.

Example 3

(1) Preparation of acidified carbon nanotube dispersion: accurately weighing 5.0 g of multi-walled carbon nanotubes (MWCNTs), 150.0 g of concentrated H$_2$SO$_4$ (98%), and 50 g of HNO$_3$ (65-68%), placing them in a three-necked flask, and heating to 100° C. for 5 hours; after the reaction is complete, conducting gradient speed centrifugation, the conditions of gradient speed centrifugation: (1) centrifugating at 1000 rpm for 10 min and filtering; (2) adding 100.0 mL of ultrapure water, centrifugating at 5000 rpm for 10 min, and filtering; (3) adding 500.0 mL of ultrapure water, centrifugating at 8000 rpm for 10 min, repeating each centrifugation step 3 times, freeze-drying to obtain the acidified carbon nanotube powder; weighing 1.0 g of the acidified carbon nanotube powder and ultrasonicating it in 50 mL of H$_2$O for 2 h to prepare 2.0% (m/v) acidified carbon nanotube dispersion for later use;

(2) Preparation of acidified carbon nanotube/PEDOT:PSS composite dispersion: accurately measuring 25.0 mL of ultrapure water in a single-necked flask, and accurately pipetting 5.0 mL of PEDOT:PSS solution and 1.0 mL of 2.0% acidified carbon nanotube dispersion into the flask, ultrasonicating at 100 W, 40 kHz for 120 min;

(3) Preparation of gelatin-based composite conductive gel solution: accurately weighing 10.0 g of gelatin and adding mixture of step (2), heating up to 60° C., stirring at constant temperature for 120 minutes to completely dissolving the gelatin and uniformly disperse the resulted mixture;

(4) Preparation of 1-(3-dimethylaminopropyl)-3-ethylcarbodiimide hydrochloride (EDC) cross-linked gelatin-based composite conductive gel: accurately weighing 0.5 g of EDC powder and dissolving it in 1 mL of H$_2$O to obtain 50% (m/v) EDC solution; accurately pipetting 1.0 mL of 50% EDC solution and slowly adding into the composite solution system of step 3, and continuing to stir at a constant temperature for 120 minutes to obtain an EDC crosslinked modified gelatin-based composite conductive gel solution;

(5) Pouring the conductive gel solution of step (4) into a custom-made polytetrafluoroethylene mold, and placing it in a refrigerator at 4° C. for 12 h; the soaking it in a PBS solution with a pH of 7.4 for 24 h to obtain a conductive biomimetic skin scaffold material with self-repair function.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for preparing a conductive biomimetic skin scaffold material with self-repairing function, comprising the following steps:
adding 1-(3-dimethylaminopropyl)-3-ethylcarbodiimide hydrochloride to a homogeneous dispersion of acidified carbon nanotubes, poly(3,4-ethylenedioxythiophene) polystyrene sulfonate (PEDOT:PSS), and gelatin to cross-link to obtain a conductive composite colloid; and
injecting the conductive composite colloid into a mold, aging at −4-4° C. for 12-24 hours, and then soaking in a phosphate-buffered saline (PBS) solution with a pH of 7.0-7.4 for 12-24 hours to obtain the conductive biomimetic skin scaffold material.

2. The method according to claim 1, further comprising:
dispersing 1.0-5.0 mL of a PEDOT:PSS solution and 1.0-5.0 mL of a 0.05-1.0 g/mL acidified carbon nanotube solution in 10.0-50.0 mL of water to obtain a mixture;
adding 1.0-10.0 g of gelatin to the mixture to evenly disperse the mixture;
adding 1.0-5.0 mL of a 0.02-0.5 g/mL 1-(3-dimethylaminopropyl)-3-ethylcarbodiimide hydrochloride aqueous solution to the mixture; and
stirring the mixture at 30-60° C. to obtain the conductive composite colloid.

3. The method according to claim 1, further comprising:
(1) adding 10.0-50.0 mL water, 1.0-5.0 mL a PEDOT:PSS solution, and 1.0-5.0 mL of a 0.05-1.0 g/mL acidified carbon nanotube solution to a reactor to form a mixture, and ultrasonicating the mixture at 50-100 W, 40 kHz, for 30-120 minutes;
(2) adding 5.0-20.0 g of gelatin to the mixture, stirring the mixture at 30-60° C. for 30-120 minutes to evenly disperse the mixture; and
(3) dissolving 0.1-0.5 g of 1-ethyl-3-(3-dimethylaminopropyl)carbodiimide (EDC) powder in 1.0-5.0 mL water to obtain a 0.02-0.5 g/mL EDC solution; adding 0.1-2.0 mL of the EDC solution slowly to the mixture of step (2), stirring for 30-120 minutes to at 30-60° C. to obtain the conductive composite colloid.

4. The method of claim 1, wherein the gelatin is derived from a fetal bovine acellular dermal matrix.

5. The method of claim 1, further comprising:
reacting 1.0-5.0 g of multi-walled carbon nanotubes, 50.0-250.0 g of 98% concentrated $H_2SO_4$, and 20.0-100.0 g of 65-68% $HNO_3$ at 50-100° C. for 5-15 hours to obtain an acidified carbon nanotube solution.

6. The method of claim 5, further comprising:
centrifugating the acidified carbon nanotube solution at a speed of 1000 to 5000 rpm for 10-60 minutes, and filtering;
adding 100.0-500.0 mL of water, centrifugating at 5000-8000 rpm for 10-60 minutes, and filtering;
adding 100.0-500.0 mL of water, centrifugating at 8000-10000 rpm for 10-60 minutes; and
freeze-drying to obtain the acidified carbon nanotubes.

* * * * *